United States Patent
Reinecke et al.

(10) Patent No.: US 7,070,572 B2
(45) Date of Patent: Jul. 4, 2006

(54) DYNAMICALLY ADJUSTABLE STABILIZATION BRACE

(75) Inventors: Steven M. Reinecke, Dallas, TX (US); Richard A. Thompson, Minneapolis, MN (US)

(73) Assignee: AMEI Technologies Inc., Wilmington, DE (US)

( * ) Notice: Subject to any disclaimer, the term of this patent is extended or adjusted under 35 U.S.C. 154(b) by 170 days.

(21) Appl. No.: 10/407,052

(22) Filed: Apr. 3, 2003

(65) Prior Publication Data

US 2004/0077983 A1 Apr. 22, 2004

Related U.S. Application Data (60) Provisional application No. 60/419,809, filed on Oct. 17, 2002.

(51) Int. Cl.
*A61F 5/00* (2006.01)

(52) U.S. Cl. .............................................. 602/5; 602/19
(58) Field of Classification Search ................ 128/845, 128/846, 869, 874, 875; 602/5, 19
See application file for complete search history.

(56) References Cited

U.S. PATENT DOCUMENTS

| | | | |
|---|---|---|---|
| 1,589,670 A | | 6/1926 | Vartia |
| 1,722,205 A | * | 7/1929 | Freund |
| 2,835,247 A | | 5/1958 | Stabholc .................... 128/78 |
| 2,886,031 A | * | 5/1959 | Robbins |
| 3,029,810 A | * | 4/1962 | Martin |
| 3,351,053 A | | 11/1967 | Stuttle ....................... 128/78 |
| 3,420,230 A | | 1/1969 | Ballard ...................... 128/75 |
| 3,521,623 A | | 7/1970 | Nichols et al. ............ 128/78 |
| 3,548,817 A | * | 12/1970 | Mittasch |
| 3,598,114 A | | 8/1971 | Lewis ........................ 128/78 |
| 3,889,664 A | * | 6/1975 | Heuser |
| 3,926,182 A | | 12/1975 | Stabholz .................... 128/75 |
| 4,135,503 A | | 1/1979 | Romano ..................... 128/78 |
| 4,178,922 A | | 12/1979 | Curlee | |
| 4,269,179 A | | 5/1981 | Burton et al. ............. 128/75 |

(Continued)

FOREIGN PATENT DOCUMENTS

| | | |
|---|---|---|
| DE | 2637244 A1 | 6/1977 |
| DE | 19610018 A1 | 10/1996 |
| EP | 0864308 A1 | 9/1998 |
| WO | WO 02/069858 A1 | 9/2002 |

OTHER PUBLICATIONS

Unknown, "Office, Computer and Industrial Ergonomics," AliMed, Dedham, Massachusetts, 2 page brochure, 1993.
Unknown, "1992 Catalog," The Saunders Group, Inc., brochure, 2 pages, 1992.
Unknown, "Catalog for Rehabilitation Professionals," Flaghouse Rehab., 2 pages, undated.
Reinecke et al., "Traction Device," U.S. Appl. No. 09/875, 486, pending, Jun. 5, 2001.

(Continued)

*Primary Examiner*—Michael A. Brown
(74) *Attorney, Agent, or Firm*—Baker & McKenzie (57) ABSTRACT

In one embodiment, a stabilization brace includes an upper belt configured to be positioned around a portion of a user's body, a lower belt configured to be positioned around the portion of the user's body, and one or more supports coupled between the upper and lower belts. Each support includes a housing, a piston slidably engaged with the housing, and a motion limiter adjustably coupled to the housing in one of a plurality of predetermined positions, the support operable to limit flexion of the portion of the user's body to a predetermined range according to the position of the motion limiter.

24 Claims, 5 Drawing Sheets

U.S. PATENT DOCUMENTS

| | | |
|---|---|---|
| 4,497,517 A | 2/1985 | Gmeiner et al. .............. 297/231 |
| 4,552,135 A | 11/1985 | Racz et al. .................... 128/78 |
| 4,559,933 A | 12/1985 | Batard et al. .................. 128/78 |
| 4,599,998 A | 7/1986 | Castillo ........................ 128/77 |
| 4,622,957 A | 11/1986 | Curlee .......................... 128/78 |
| 4,682,587 A | 7/1987 | Curlee |
| 4,682,588 A | 7/1987 | Curlee .......................... 128/78 |
| 4,685,668 A | 8/1987 | Newlin, Jr. .................. 272/123 |
| 4,691,696 A | 9/1987 | Farfan de los Godos ..... 128/78 |
| 4,702,235 A | 10/1987 | Hong ............................ 128/78 |
| 4,715,362 A * | 12/1987 | Scott |
| 4,721,102 A | 1/1988 | Pethybridge ................. 128/78 |
| 4,836,194 A | 6/1989 | Sebastian et al. ............. 128/78 |
| 4,884,562 A | 12/1989 | Stone ........................... 128/78 |
| 4,898,185 A | 2/1990 | Fuller .......................... 128/876 |
| 4,907,575 A | 3/1990 | Satterthwaite ............... 128/75 |
| 4,991,572 A | 2/1991 | Chases ........................ 128/75 |
| 4,991,573 A | 2/1991 | Miller .......................... 128/78 |
| 5,060,640 A | 10/1991 | Rasmusson ............... 128/80 C |
| 5,062,414 A | 11/1991 | Grim .......................... 128/68.1 |
| 5,111,807 A | 5/1992 | Spahn et al. ................ 606/244 |
| 5,144,943 A | 9/1992 | Luttrell et al. ............ 128/25 B |
| 5,188,586 A | 2/1993 | Castel et al. .................. 602/19 |
| 5,195,948 A | 3/1993 | Hill et al. |
| 5,207,635 A | 5/1993 | Richards et al. .............. 602/19 |
| 5,256,135 A | 10/1993 | Avihod ......................... 602/19 |
| 5,363,863 A | 11/1994 | Lelli et al. .................. 128/876 |
| 5,382,226 A | 1/1995 | Graham ........................ 602/32 |
| RE34,883 E | 3/1995 | Grim |
| 5,403,266 A | 4/1995 | Bragg et al. .................... 602/5 |
| 5,437,615 A | 8/1995 | Pekar et al. |
| 5,437,617 A | 8/1995 | Heinz et al. .................. 602/19 |
| 5,441,479 A | 8/1995 | Chitwood .................... 602/18 |
| 5,450,858 A | 9/1995 | Zablotsky et al. |
| 5,462,518 A | 10/1995 | Hatley et al. ................. 602/36 |
| 5,586,969 A | 12/1996 | Yewer, Jr. .................... 602/19 |
| 5,651,764 A | 7/1997 | Chiu ............................. 602/36 |
| 5,681,267 A | 10/1997 | Molino et al. ................ 602/19 |
| 5,690,609 A | 11/1997 | Heinze, III ................... 602/19 |
| 5,695,452 A | 12/1997 | Grim et al. |
| 5,722,940 A | 3/1998 | Gaylord, Jr. et al. ......... 602/19 |
| 5,913,410 A | 6/1999 | Tsuchiya ........................ 2/311 |
| 5,916,188 A | 6/1999 | Ousdal ......................... 602/32 |
| 5,950,628 A | 9/1999 | Dunfee |
| 6,099,490 A | 8/2000 | Turtzo .......................... 602/19 |
| 6,146,345 A | 11/2000 | Mignard ...................... 602/19 |
| 6,331,170 B1 | 12/2001 | Ordway |
| 6,364,186 B1 | 4/2002 | Gilmour et al. |
| 6,533,740 B1 | 3/2003 | Reinecke et al. |
| 6,540,707 B1 | 4/2003 | Stark et al. |

OTHER PUBLICATIONS

Reinecke et al., "Canting Mechanism for an Ambulatory Support Device," U.S. Appl. No. 09/875,473, pending, Jun. 5, 2001.

Reinecke et al., "Traction Device Adjustment Mechanism and Method," U.S. Appl. No. 09/875,315, pending, Jun. 5, 2001.

Reinecke et al., "Measurement Device for Fitting a Bracing Device," U.S. Appl. No. 10/154,695, pending, May 23, 2002.

Reinecke et al., "Ambulatory Cyclic Traction Device," U.S. Appl. No. 10/370,823, pending, Feb. 20, 2003.

Reinecke et al., "Traction Device and Associated Lifting Mechanisms," U.S. Appl. No. 10/335,694, pending, Jan. 2, 2003.

PCT, Notification of Transmittal of the International Search Report or the Declaration, 6 pages, Apr. 7, 2002.

PCT, Notification of Transmittal of the International Search Report or the Declaration, 6 pages, Apr. 7, 2002.

PCT, Notification of Transmittal of the International Search Report or the Declaration, 7 pages, Apr. 7, 2002.

PCT, Notification of Transmittal of the International Search Report or the Declaration, 6 pages, Apr. 7, 2002.

PCT, Notification of Transmittal of the International Search Report or the Declaration, 6 pages, Jan. 31, 2003.

PCT, Notification of International Search Report or the Declaration and International Search Report for PCT/US03/32266, Sep. 3, 2004, 4 pages.

* cited by examiner

DYNAMICALLY ADJUSTABLE STABILIZATION BRACE

RELATED APPLICATIONS

This application claims the benefit under 35 U.S.C. §119(e) of U.S. Provisional Application Ser. No. 60/419,809 filed Oct. 17, 2002 entitled "Dynamically Adjustable Stabilization Brace."

TECHNICAL FIELD OF THE INVENTION

This invention relates to the field of medical devices and, more particularly, to a dynamically adjustable stabilization brace.

BACKGROUND OF THE INVENTION

People have long dealt with the pain, aggravation, and loss of productivity arising from bodily injuries, such as those to the back, knees, and elbows. In fact most people will at some point in their lives be at least temporarily incapacitated by back pain, particularly low back pain. The relative ease with which injuries to the back and other portions of the body are incurred merely adds to the overall severity of the problem of dealing with bodily injuries. The forms of treatment vary over the length of time that a patient experiences pain. For example, eighty percent of low back pain sufferers heal over the course of six weeks with minimal intervention. However, the remaining twenty percent of sufferers create the greatest challenges and cost to the medical system. After the acute phase, surgical intervention or more invasive forms of treatment may be selected. However, minimally-invasive or non-invasive treatment methods are preferred. Another concern when dealing with bodily injuries is rehabilitation. Because injuries to the back, knees, elbows, and other portions of the body do not typically heal within a day or two, effective methods of rehabilitation are important for recovery.

SUMMARY OF THE INVENTION

According to the present invention, disadvantages and problems associated with previous techniques for rehabilitating injuries may be reduced or eliminated.

In one embodiment, a stabilization brace includes an upper belt configured to be positioned around a portion of a user's body, a lower belt configured to be positioned around the portion of the user's body, and one or more supports coupled between the upper and lower belts. Each support includes a housing, a piston slidably engaged with the housing, and a motion limiter adjustably coupled to the housing in one of a plurality of predetermined positions, the support operable to limit flexion of the portion of the user's body to a predetermined range according to the position of the motion limiter.

In another embodiment, a method for fitting a user for a stabilization brace includes positioning a backplate of the stabilization brace on a user, the backplate having a first pair of canting mechanisms associated with a first side of the backplate and a second pair of canting mechanisms associated with a second side of the backplate. An upper main belt and an upper secondary belt are positioned around a first portion of the user's body, a lower main belt and a lower secondary belt are positioned around a second portion of the user's body, and a desired length of each of the main belts is determined based on the first and second portions of the user's body. Each of the main belts is conformed to their determined desired lengths, a first end of each of the main and secondary belts is coupled to a corresponding canting mechanism, the upper main and secondary belts are allowed to adjust to conform to an underlying structure and natural conical shape of the first portion of the user's body through rotation of the corresponding canting mechanisms, and the lower main and secondary belts are allowed to adjust to conform to an underlying structure and natural conical shape of the second portion of the user's body through rotation of the corresponding canting mechanisms. The canting mechanisms are secured to prevent further rotation of the canting mechanisms, a second end of the upper main belt is coupled to a second end of the upper secondary belt, and a second end of the lower main belt is coupled to a second end of the lower secondary belt.

In another embodiment, a canting system for a stabilization brace having two belts includes a backplate configured to be coupled between opposing ends of each of the belts and includes a plurality of canting mechanisms rotatably coupled to the backplate. Each canting mechanism is operable to couple an end of a corresponding belt to the backplate. Each canting mechanism includes a buckle base rotatably coupled to the backplate, the buckle base operable to receive the end of the corresponding belt and to allow the end to rotate about an associated pivot to allow the belt to conform to a portion of the user's body, and includes a buckle lever coupled to the buckle base and operable to secure the end of the corresponding belt against the buckle base to prevent the buckle base from rotating once the belt has conformed to the portion of the user's body.

Certain embodiments of the present invention may provide one or more technical advantages. Certain embodiments of the invention may provide all, some, or none of these advantages. For example, certain embodiments provide a stabilization brace that allows a range of motion of the user's spine or other joint, while limiting the degree of flexion to a predetermined range, to improve healing and rehabilitation relative to techniques in which the spine or other joint is substantially immobilized using a brace or otherwise. Certain embodiments may provide resistance against such flexion to stabilize the spine or other joint and limit bending, lifting, or other activities. In certain embodiments, the predetermined range of flexion, the resistance provided against such flexion, or both, may be adjusted according to particular needs. Such adjustability may improve the effectiveness of rehabilitation and ultimately help to wean the user off of the stabilization brace. In certain embodiments, the stabilization brace may also provide belts with canting mechanisms that allow the stabilization brace to be properly fitted for each particular user. Such canting mechanisms may rotate to allow the corresponding belts to conform to the underlying structure of the user's body, such as the natural conical shapes of the user's upper torso below the ribs and user's lower torso above the hips for example. Once a proper fit is achieved, the canting mechanisms may be locked into position to maintain the fit so that maximum comfort and effectiveness may be achieved. Stabilization braces in certain embodiments may be used in association with joints other than the spine, such as the knee, elbow, or neck for example. Furthermore, certain embodiments provide a stabilization brace that is ambulatory, meaning that the brace is portable and wearable during the user's daily activities. The ambulatory nature of the stabilization brace provides more convenience to the user, causes less impact on the user's daily activities, and perhaps most importantly promotes healing and rehabilitation relative to previous techniques. Certain embodiments may provide one or more other technical advantages, one or more of which may be readily apparent to those skilled in the art from the figures, description, and claims included herein.

BRIEF DESCRIPTION OF THE DRAWINGS

To provide a more complete understanding of the present invention and certain features and advantages thereof, reference is made to the following description taken in conjunction with the accompanying drawings, in which.

DESCRIPTION OF EXAMPLE EMBODIMENTS

Figure 1A:
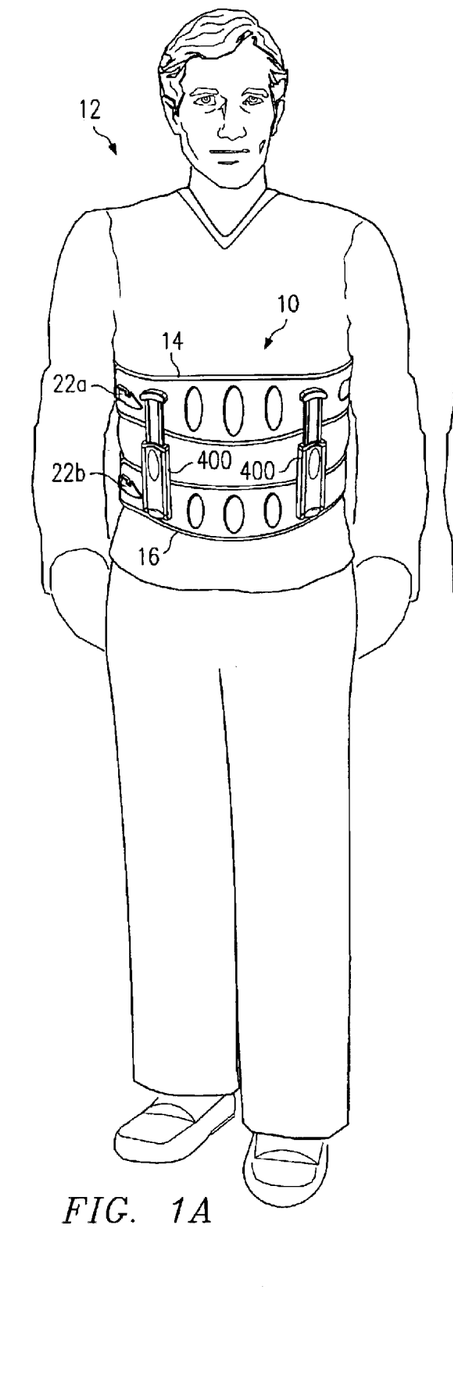
FIGS. 1A and 1B are front and rear views, respectively, illustrating a user wearing an example stabilization brace.
Figure 1B:
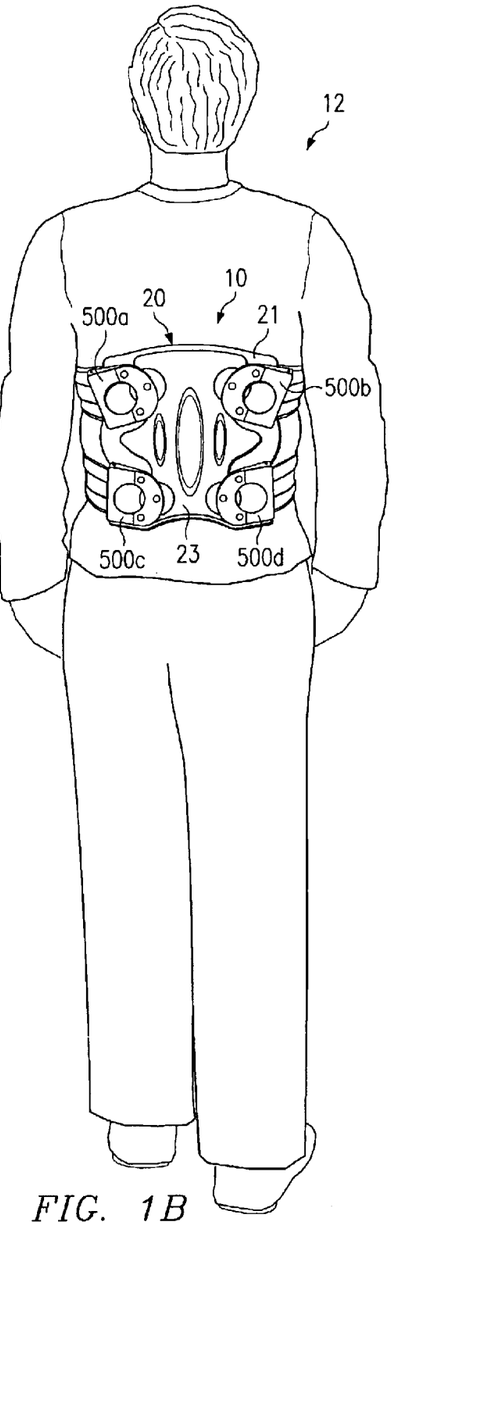

FIGS. 1A and 1B are front and rear views, respectively, illustrating a user 12 wearing an example stabilization brace 10. In the illustrated embodiment, stabilization brace 10 is operable to control the range of motion of the user's spine, limiting the degree of flexion to a predetermined range. However, in other embodiments, stabilization brace 10 may be modified to control the range of motion and limit the degree of flexion of any joint, such as the knee, elbow, or neck.

Stabilization brace 10 includes an upper belt 14 and a lower belt 16. Belts 14, 16 may be formed in any suitable manner that allows them to be positioned around a desired portion of the user's body. Example details of one embodiment of belts 14, 16 are described in greater detail below with reference to FIG. 4. In the illustrated embodiment, stabilization brace 10 also includes one or more supports 400, a backplate 20, a pair of canting mechanisms 500 associated with each support belt 14, 16, and a pair of locking mechanisms 22a, 22b associated with each support belt 14, 16.

Backplate 20, as illustrated in FIG. 1B, generally conforms to the lower back of user 12. Hence, backplate 20 may have any suitable shape and may be formed from any suitable material. In the illustrated embodiment, backplate 20 includes a foam portion 21 and a rigid portion 23. Foam portion 21 may have any suitable thickness, and functions to provide comfort to user 12 when user 12 is wearing stabilization brace 10. Rigid portion 23, which may be formed from any suitable material, functions to provide support to the lower back of user 12 and, as described in further detail below, to support canting mechanisms 500 that couple to ends of belts 14, 16. Foam portion 21 and rigid portion 23 may be coupled together in any suitable manner, such as through adhesive coupling, mechanical coupling, or any other suitable joining process. Backplate 20 may incorporate an integrated pneumatic or other fluidic lumbar pad to provide increased comfort and lumbar support.

Figure 2A:
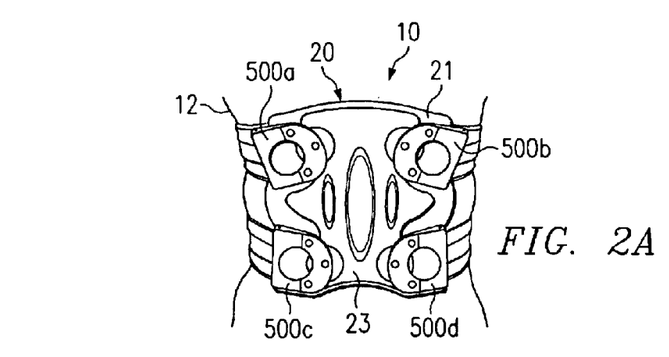
FIGS. 2A and 2B illustrate examples in which canting mechanisms allow corresponding belts to conform to the underlying structure and natural conical shapes of a particular user's body.
Figure 2B:
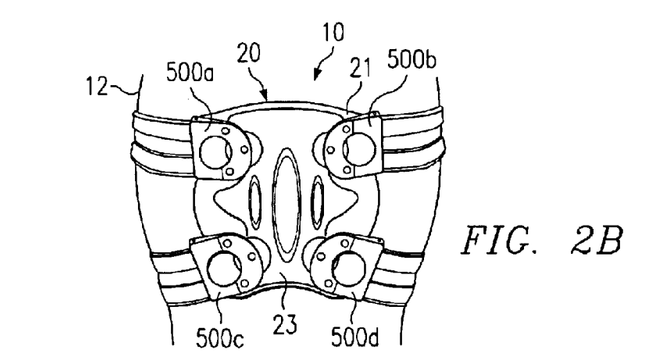

Canting mechanisms 500 are described in greater detail below with reference to FIGS. 6A and 6B. Generally, canting mechanisms 500 couple corresponding portions of belts 14, 16 to backplate 20 and ensure that belts 14, 16 conform to the user's body in a correct and comfortable manner. For example, as shown in FIGS. 2A and 2B, canting mechanisms 500 preferably allow belts 14, 16 to conform to the underlying structure and natural conical shapes of the particular user's upper torso below the ribs (upper belt 14) and lower torso above the hips (lower belt 16). FIG. 2A illustrates belts 14, 16 conformed to a user 12 having a relatively thin mid-section, while FIG. 2B illustrates belts 14, 16 conformed to a user 12 having a relatively thick mid-section, canting mechanisms 500 providing for a correct and comfortable fit in either situation. Details regarding one method of fitting stabilization brace 10 to user 12 using canting mechanisms 500 is described below with reference to FIG. 7.

Referring again to FIG. 1, to secure upper belt 14 and lower belt 16 around the user's body, locking mechanisms 22a and 22b, respectively, are utilized. As described in greater detail below with reference to FIG. 4, in one embodiment each locking mechanism 22 includes a notched strap 30 having a number of notches and a latch 32 for securing locking mechanism 22 in place in a desired notched location after the corresponding belt 14, 16 has been positioned around the user's body. Locking mechanisms 22 may be replaced with any suitable mechanism for securing belts 14, 16 in a desired location, such as snaps, hook and loop type fasteners, or other suitable mechanisms.

As described in greater detail below with reference to FIG. 5, in one embodiment supports 400 each include a motion limiter 408 that controls the range of motion of the user's spine, limiting the degree of flexion to a predetermined, preferably adjustable, range based on the location of motion limiter 408. Supports 400 may also each include one or more elastic members 406 that provide a predetermined, preferably adjustable, level of resistance against flexion of the user's spine based on the elasticity and number of elastic members 406 used. Coupling of supports 400 to belts 14, 16 may be accomplished in any suitable manner, such as through adhesive coupling, mechanical coupling, or any other suitable technique. Example locations of supports 400 about the circumference of belts 14, 16 are further illustrated in FIG. 3.

In operation, in one embodiment, user 12 is fitted for stabilization brace 10 as described below in conjunction with FIG. 7. After being properly fitted for stabilization brace 10, user 12 positions stabilization brace 10 around the user's torso, adjusts belts 14, 16 to a desired tension, and allows belts 14, 16 to conform to the user's underlying structure and natural conical shapes using canting mechanisms 500. User 12 may then secure belts 14, 16 in place using locking mechanisms 22. Because supports 400 are positioned near the abdomen of user 12, supports 400 are able to control the motion of the user's spine, limiting the degree of flexion to a predetermined range and preferably also providing a predetermined level of resistance against such flexion. Depending on the location of motion limiter 408 (FIG. 5) and the elasticity of elastic member 406 (FIG. 5), user 12 is prevented from bending forward too far, encounters resistance while bending forward, or preferably both. As described in greater detail below, the maximum degree of flexion may be adjustable, the amount of resistance encountered may be adjustable, or both. Stabilization brace 10 may be ambulatory, being portable and wearable during everyday activities. As such, stabilization brace 10 may be applied at home, at work, at play, or during travel at the convenience of user 12. Therefore, user 12 may be more likely to comply with rehabilitation guidelines than if user 12 is required to travel to a clinic for rehabilitation.

Figure 3:
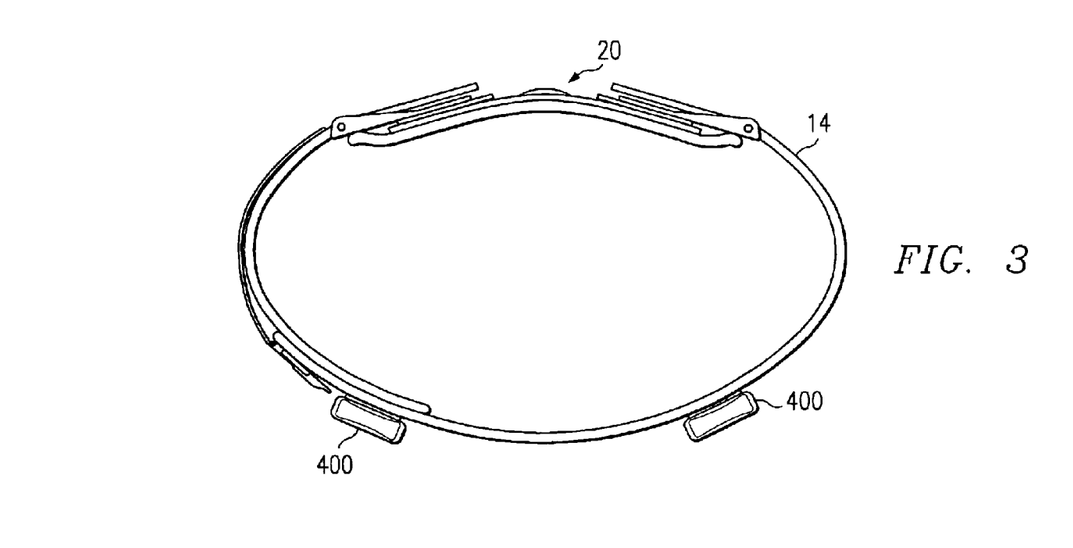
FIG. 3 is a top plan view illustrating an example stabilization brace showing example locations for supports for limiting a user's degree of flexion to a predetermined range.

FIG. 3 is a top plan view illustrating an example stabilization brace 10 showing example locations for supports 400. In FIG. 3, two supports 400 are shown in a location that generally corresponds to the front of the user's body near the abdomen. However, there may be any suitable number of supports 400 and they may be located at any suitable locations around the circumference of belts 14, 16. For example, if side-to-side flexion of user 12 is a concern, then supports 400 may be located towards the sides of belts 14, 16.

Figure 4:
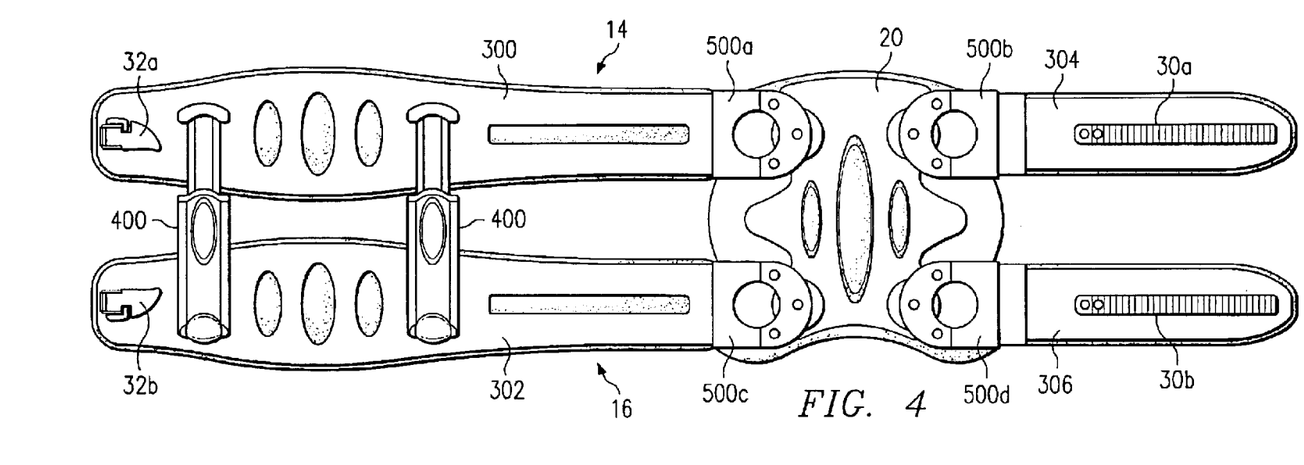
FIG. 4 is a schematic view illustrating example upper and lower belts of a stabilization brace.

FIG. 4 is a schematic view illustrating example upper belt 14 and lower belt 16. As illustrated in FIG. 4, in one embodiment, upper belt 14 includes an upper main belt 300 and an upper secondary belt 304. Similarly, lower belt 16 includes a lower main belt 302 and a lower secondary belt 306. All portions of belts 14, 16 may be formed from any suitable material. In the illustrated embodiment, all portions of belts 14, 16 have foam portions and rigid portions similar to backplate 20. The foam portions and rigid portions may be coupled in any suitable manner, such as through adhesive or mechanical coupling. The foam portions and rigid portions may also have any suitable size and shape. In addition, the spacing of upper belt 14 from lower belt 16 may be any spacing suitable for the size and shape of user 12.

In one embodiment, upper main belt 300 is coupled to an upper portion of backplate 20 by canting mechanism 500a at one end and includes latch 32a of locking mechanism 22a at the other end. Upper secondary belt 304 is coupled to the upper portion of backplate 20 opposite upper main belt 300 by canting mechanism 500b. Upper secondary belt 304 also includes notched strap 30a of locking mechanism 22a. As a result, when stabilization brace 10 is positioned around user 12, notched strap 30a and latch 32a will preferably coincide with one another at a particular location around the circumference of the user's body. The lengths of upper main belt 300 and upper secondary belt 304 may be determined during the fitting of stabilization brace for a particular user 12. One embodiment of this fitting is described in greater detail below with reference to FIG. 7. The coupling of upper main belt 300 and upper secondary belt 304 to backplate 20 by canting mechanisms 500a, 500b is described in further detail below with reference to FIGS. 6A and 6B.

In one embodiment, lower main belt 302, similar to upper main belt 300, includes latch 32b of locking mechanism 22b at one end and is coupled to a lower portion of backplate 20 at the other end by canting mechanism 500c. Lower secondary belt 306, similar to upper secondary belt 304, includes notched strap 30b at one end and is coupled opposite lower main belt 302 to the lower portion of backplate at the other end by canting mechanism 500d. The lengths of lower main belt 302 and lower secondary belt 306 may be determined during the fitting of stabilization brace 10 for a particular user 12, as for upper main belt 300 and upper secondary belt 304.

Also shown in FIG. 4 are supports 400 coupled between upper main belt 300 and lower main belt 302. Again, supports 400 may be coupled to upper main belt 300 and lower main belt 302 in any suitable manner.

Figure 5:
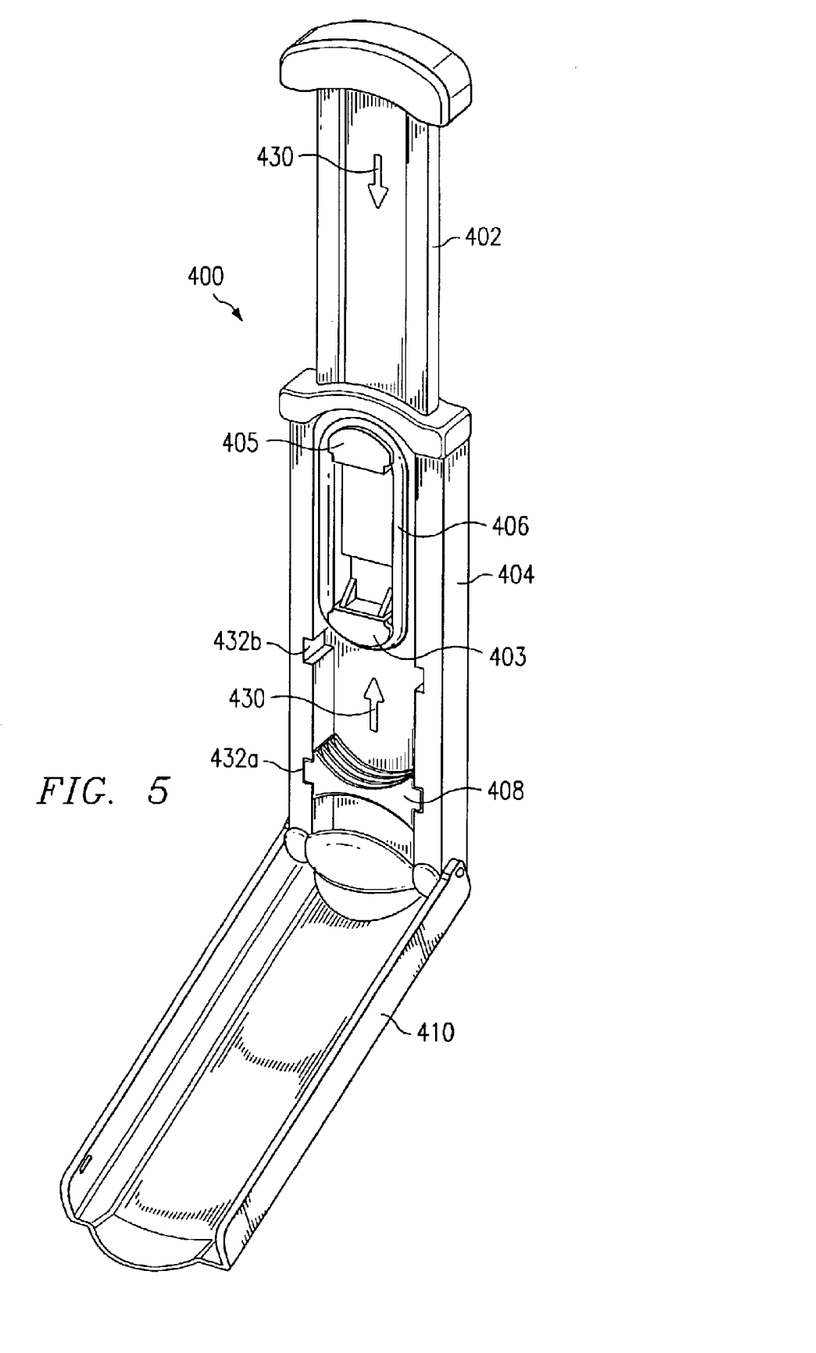
FIG. 5 illustrates an example support for limiting a user's degree of flexion to a predetermined range.

FIG. 5 illustrates an example support 400. Other suitable supports may be utilized in other embodiments. In one embodiment, support 400 includes a piston 402 having a protuberance 403, a housing 404 having a protuberance 405, an elastic member 406 coupled between protuberance 403 and protuberance 405, a motion limiter 408, and a piston cover 410. Support 400 is shown in a generally uncompressed state that corresponds to a generally upright position of user 12. As user 12 bends forward, piston 402 and housing 404 move in the directions of arrows 430. This movement forces elastic member 406 to elongate, which provides a force resisting user 12 from bending forward. The amount of this resistance depends on the elasticity and number of elastic members 406 used. Piston 402 may eventually reach a stopping point, which is dictated by the position of motion limiter 408.

Piston 402 and housing 404 may have any suitable size and shape and may be formed from any suitable material, although support 400 preferably maintains a low profile against the user's body for comfort, wearability, and aesthetic purposes. Piston 402 may be coupled to upper belt 14 in any suitable manner and housing 404 may be coupled to lower belt 16 in any suitable manner. Protuberance 403 may be formed integral with piston 402 or may be a separate element coupled to piston 402 in any suitable manner. Similarly, protuberance 405 may be formed integral with piston housing 404 or may be a separate element coupled to piston housing 404 in any suitable manner. Although protuberances 403 and 405 may have any suitable shape, they are configured to provide secure engagement with elastic member 406. The distance between protuberances 403 and 405 when support 400 is in a generally uncompressed state may be any suitable distance.

Elastic member 406 may be an elastomer formed from any suitable elastomeric material. Elastic member 406, as illustrated in FIG. 5, fits around protuberance 403 at one end and around protuberance 405 at the other end. Elastic member 406 should preferably conform to its natural shape when installed around protuberances 403 and 405 such that there is no slack therein which would effect the resistance that user 12 feels when bending forward. Elastic member 406 may be interchangeable with other elastic members 406 having different elasticities, as a result of their thicknesses or the inherent elasticities of the elastomeric materials from which they are formed, to control the amount of resistance encountered. There may be more than one elastic member 406 simultaneously disposed around protuberances 403 and 405. In an embodiment where multiple elastic members 406 may be utilized simultaneously, one or more elastic member 406 may be selectively installed or removed to increase or decrease, respectively, the amount of resistance encountered.

Motion limiter 408 may be formed from any suitable material and may couple to housing 404 in any suitable manner. In one embodiment, motion limiter 408 removably couples to housing 404 using a pair of motion limiter grooves 432a. The position of motion limiter 408 is adjustable with respect to housing 404 depending on the desired stopping position for piston 402. For example, motion limiter 408 may be removably coupled to housing 404 at a pair of motion limiter grooves 432b that corresponds to zero travel for piston 402 or motion limiter 408 may be removably coupled to housing 404 using motion limiter grooves 432a (as illustrated) that allow for some predetermined travel for piston 402. In a particular embodiment, motion limiter 408 may be removed completely such that the bottom of housing 404 is used as a stop. Grooves 432 may be formed in piston housing 404 at any suitable location and there may be any suitable number of grooves formed therein.

Cover 410 may be coupled to housing 404 in any suitable manner; however, in one embodiment, cover 410 is hinged to housing 404. Cover 410 facilitates access to the inside of housing 404 so that elastic member 406 may be readily removed and/or replaced and so that motion limiter 408 may be moved and/or removed. As described above, any number of supports 400 may be used around the circumference of stabilization brace 10 to control the degree of flexion of the user's spine in any number of directions.

Figure 6A:
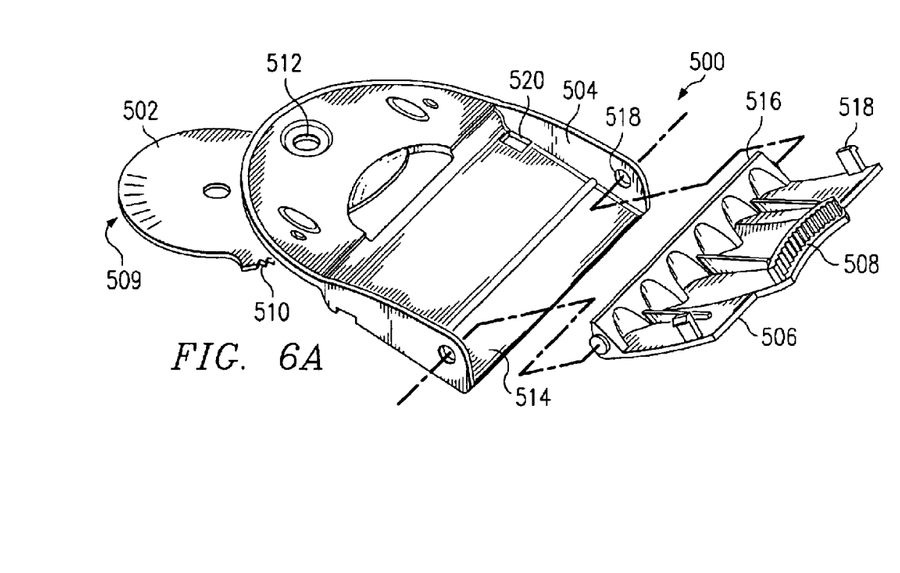
FIG. 6A illustrates an example canting mechanism.

FIG. 6A illustrates an example canting mechanism 500. As described above, canting mechanisms 500 couple ends of belts 14, 16 to backplate 20 and help ensure that belts 14, 16 conform to the underlying structure and natural conical shapes of the user's body to provide a correct and comfortable fit. Accordingly, in one embodiment, a portion of each belt 14, 16 is secured within a buckle base 504 with a buckle lever 506, which is shown in FIG. 6A to be hingedly coupled to buckle base 504 at a pivot 518. Buckle base 504 may have any suitable shape and may be formed from any suitable material. Buckle base 504 includes a receptacle 514 to accept an end of belt 14, 16. Buckle base 504 also includes a pair of notches 520 formed therein to accept a pair of latches 518 on buckle lever 506 so that buckle lever 506 may be securely engaged with buckle base 504 to hold the end of belt 14, 16 within receptacle 514. Buckle lever 506 functions to secure the end of belt 14, 16 within receptacle 514 with a protrusion 516 near one of its ends. Buckle lever 506 may have any suitable shape and may be formed from any suitable material.

In the illustrated embodiment, buckle base 504 is rotatably coupled to backplate 20 at pivot 512 in a suitable manner, such as through mechanical coupling. This rotatable coupling allows belt 14, 16 to rotate about pivot 512 to conform to the user's body. Once the desired degree of cant is achieved, then buckle lever 506 is closed to secure belt 14, 16 within receptacle 514 of buckle base 504. The closure of buckle lever 506 prevents canting mechanism 500 from rotating once the desired degree of cant is achieved. This is accomplished with the help of a buckle locking disc 502.

Buckle locking disc 502 may be coupled to backplate 20 in any suitable manner. In addition, buckle locking disc 502 may be rotatably coupled to buckle base 504 at pivot 512. Buckle locking disc 502, which may have any suitable shape and may be formed from any suitable material, may include one or more canting indicators 509 that function to indicate the degree of cant to a person that is fitting stabilization brace 10 for user 12. Once the desired degree of cant is achieved, buckle base 504 and buckle lever 506 may be prevented from rotating by engaging buckle lever 506 with buckle locking disc 502. Buckle locking disc 502 includes a set of gear teeth 510 that mesh with a set of gear teeth 508 on buckle lever 506 when buckle lever 506 is in a closed position. This meshing of gear teeth 508 and gear teeth 510 locks buckle base 504 in place so that buckle base 504 is unable to rotate with respect to backplate 20. This meshing is illustrated in FIG. 6B, which is a view of canting mechanism 500 from the back side.

Figure 6B:
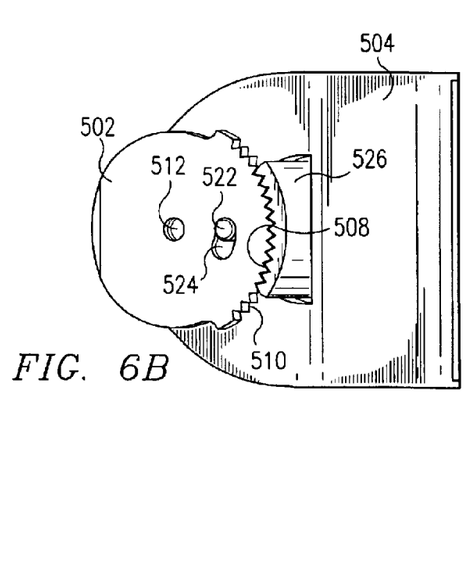
FIG. 6B is a perspective view of the example canting mechanism of FIG. 6A illustrating the interaction between an example buckle locking disc and an example buckle base of the canting mechanism.

Referring to FIG. 6B, the set of gear teeth 508 on buckle lever 506 is shown meshed with the set of gear teeth 510 on buckle locking disc 502. The meshing may be facilitated by an opening 526 formed in buckle base 504. Also shown is a protuberance 522 coupled to the underside of buckle base 504 that engages a slot 524 formed in buckle locking disc 502. The length of slot 524 determines how much rotation of buckle base 504 is allowed before buckle base 504 is prevented from rotating by the meshing of gear teeth 508 and gear teeth 510.

Figure 7:
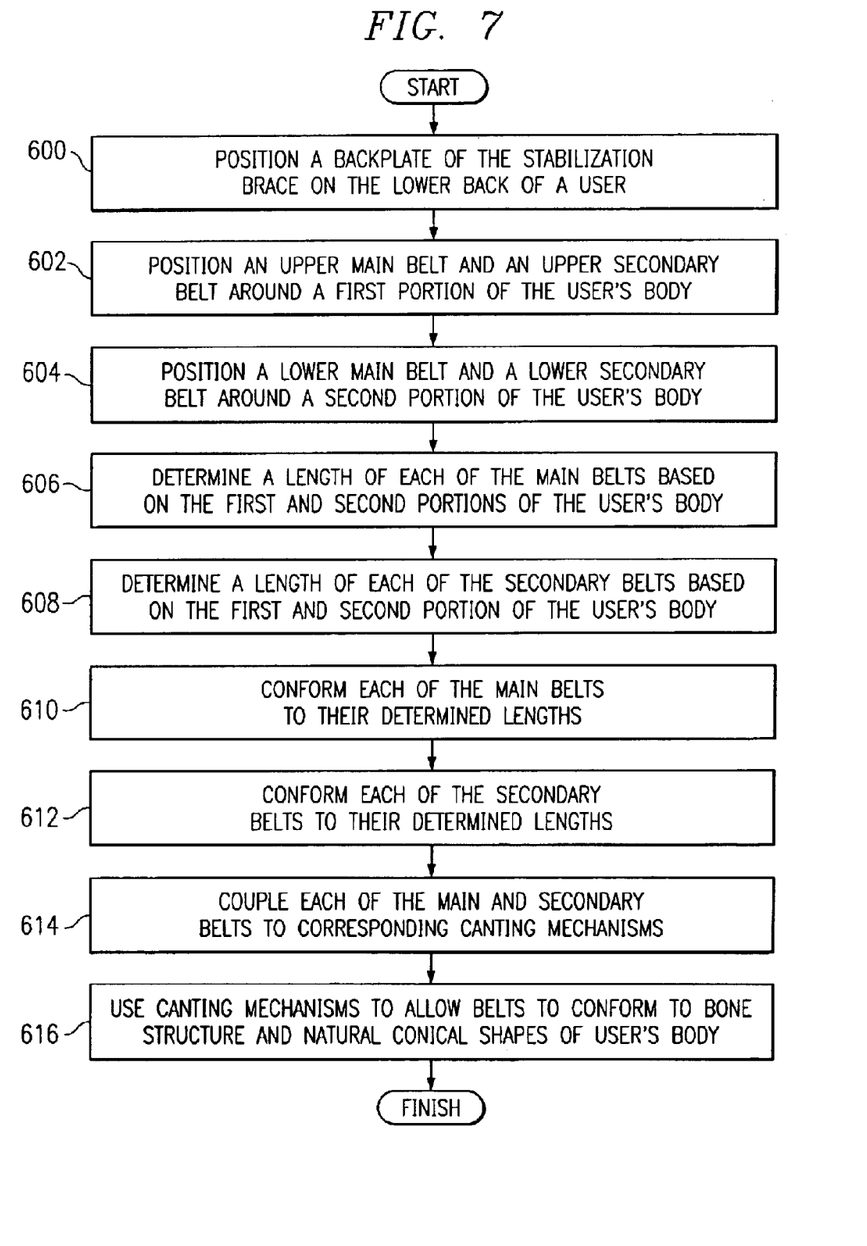
FIG. 7 illustrates an example method for fitting a user for a stabilization brace.

FIG. 7 illustrates an example method for fitting user 12 for stabilization brace 10. Upper belt 14 and lower belt 16 of stabilization brace 10 may be fitted concurrently in some embodiments or consecutively in other embodiments. The example method begins at step 600 where backplate 20 of stabilization brace 10 is positioned on the lower back of user 12. Backplate 20 includes a first pair of canting mechanisms 500 coupled to a first side of backplate 20 and a second pair of canting mechanisms 500 coupled to a second side of backplate 20. Upper main belt 300 and upper secondary belt 304 are positioned around a first portion of user 12 at step 602. Lower main belt 302 and lower secondary belt 306 are positioned around a second portion of user 12 at step 604.

In one embodiment, belts 14, 16 are provided with lengths that can accommodate the largest typical user 12. For smaller users 12, portions of belts 14, 16 may be reduced in length to fit the particular user 12. Therefore, the proper lengths of belts 14, 16 need to be determined. Accordingly, at step 606, the lengths of upper main belt 300 and lower main belt 302 are determined based on the first and second portions of the user's body, respectively. For example, the first portion of the body may be the upper torso below the ribs and the second portion of the body may be the lower torso above the hips. The lengths of upper secondary belt 304 and lower secondary belt 306 may also be determined based on the first and second portions of the body, at step 608. Once the proper lengths are determined, upper main belt 300 and lower main belt 302 may be conformed to their determined lengths at step 610 and if applicable, upper secondary belt 304 and lower secondary belt 306 may be conformed to their determined lengths at step 612. In certain embodiments, this conforming may include cutting excess length of a particular belt portion. In some embodiments, not all belt portions will have to be conformed to their determined lengths because one or more belt portions may have the proper length for a particular user 12.

At step 614, upper main belt 300, lower main belt 302, upper secondary belt 304, and lower secondary belt 306 are coupled to backplate 20 using corresponding canting mechanisms 500. This may include placing an end of each of the main and secondary belts in receptacle 514 of a corresponding buckle base 504 and clamping down on the end with buckle lever 506 that is hingedly coupled to buckle base 504. Before clamping down on the end, however, at step 616 each canting mechanism 500 may be allowed to rotate about associated pivot 512 to allow its corresponding belt portion to adjust to conform to the underlying structure and natural conical shapes of the user's body. Then buckle lever 506 may be closed to secure canting mechanism 500 in its correct position. This ends the example method outlined in FIG. 7.

Although the present invention is described with several embodiments, numerous changes, substitutions, variations, alterations, and modifications may be suggested to one skilled in the art, in the intention is that the invention encompass all such changes, substitutions, variations, alterations, and modifications as falls within the spirit and scope of the appended claims.

What is claimed is:

1. A stabilization brace, comprising:
   an upper belt configured to be positioned around a portion of a user's body; and
   a lower belt configured to be positioned around the portion of the user's body; and
   one or more supports coupled between the upper and lower belts, each support comprising:

a housing:
a piston slidably engaged with the housing; and
a motion limiter adjustably coupled to the housing in one of a plurality of predetermined positions, the support operable to limit flexion of the portion of the user's body to a predetermined range according to the position of the motion limiter;
wherein the housing comprises one or more pairs of motion limiter grooves for removably coupling the motion limiter to the housing, each pair of motion limiter grooves adapted to define a predetermined position of the motion limiter and thus a predetermined range of flexion of the portion of the user's body.

2. A stabilization brace, comprising:
an upper belt configured to be positioned around a portion of a user's body; and
a lower belt configured to be positioned around the portion of the user's body; and
one or more supports coupled between the upper and lower belts, each support comprising:
a housing;
a piston slidably engaged with the housing;
a motion limiter adjustably coupled to the housing in one of a plurality of predetermined positions, the support operable to limit flexion of the portion of the user's body to a predetermined range according to the position of the motion limiter;
an elastic member coupled between the piston and the housing, the elastic member adapted to provide a predetermined resistance against flexion of the portion of the user's body; and
one or more additional elastic members removably coupled between the piston and the housing such that one or more of the additional elastic members may be removed to decrease the resistance provided.

3. A stabilization brace, comprising:
an upper belt configured to be positioned around a portion of a user's body; and
a lower belt configured to be positioned around the portion of the user's body; and
one or more supports coupled between the upper and lower belts, each support comprising:
a housing:
a piston slidably engaged with the housing; and
a motion limiter adjustably coupled to the housing in one of a plurality of predetermined positions, the support operable to limit flexion of the portion of the user's body to a predetermined range according to the position of the motion limiter;
wherein the stabilization brace further comprises a backplate coupled between the upper and lower belts, an upper portion of the backplate coupled to the upper belt using a first pair of canting mechanisms, a lower portion of the backplate coupled to the lower belt using a second pair of canting mechanisms, each pair of canting mechanisms operable to allow the corresponding upper or lower belt to adjust to conform to underlying structure and natural conical shapes of the user's body.

4. The stabilization brace of claim 3, wherein each canting mechanism comprises:
a buckle locking disc coupled to the backplate;
a buckle base rotatably coupled to the buckle locking disc, the buckle base operable to allow an end of the corresponding upper or lower belt to rotate about an associated pivot to allow the belt to conform to the portion of the user's body; and
a buckle lever coupled to the buckle base and operable to secure the end of the corresponding belt against the buckle base to prevent the buckle base from rotating once the belt has conformed to the portion of the user's body.

5. The stabilization brace of claim 4, wherein: the buckle locking disc is coupled between the backplate and the buckle base; and
the buckle locking disc comprises a first set of gear teeth configured to mesh with a second set of gear teeth on the buckle lever when the buckle lever is in a closed position such that the buckle base is no longer able to rotate with respect to the backplate.

6. A stabilization brace, comprising:
an upper belt configured to be positioned around a portion of a user's body and
a lower belt configured to be positioned around the portion of the user's body; and
one or more supports coupled between the upper and lower belts, each support comprising:
a housing:
a piston slidably engaged with the housing and
a motion limiter adjustably coupled to the housing in one of a plurality of predetermined positions, the support operable to limit flexion of the portion of the user's body to a predetermined range according to the position of the motion limiter;
wherein the stabilization brace further comprises a housing cover hingedly coupled to the housing to provide access for adjustment of the motion limiter to another one of the plurality of predetermined positions.

7. A stabilization brace, comprising:
an upper belt configured to be positioned around a portion of a user's body; and
a lower belt configured to be positioned around the portion of the user's body; and
one or more supports coupled between the upper and lower belts, each support comprising:
a housing comprising a plurality of pairs of motion limiter grooves;
a piston slidably engaged with the housing;
a motion limiter adjustably coupled to the housing in one of a plurality of predetermined positions using one of the plurality of pairs of motion limiter grooves, each pair of motion limiter grooves defining a predetermined position of the motion limiter and thus a predetermined range of flexion of the portion of the user's body, the support operable to limit flexion of the portion of the user's body to a predetermined range according to the position of the motion limiter;
an elastic member removably coupled between the piston and the housing, the elastic member adapted to provide a predetermined resistance against flexion of the portion of the user's body, the elastic member able to be replaced with another elastic member having a different elasticity to adjust the resistance provided; and
a housing cover hingedly coupled to the housing to provide access for adjustment of the motion limiter to another one of the plurality of predetermined positions.

8. A method for fitting a user for a stabilization brace, comprising:
positioning a backplate of the stabilization brace on a user, the backplate having a first pair of canting mechanisms associated with a first side of the backplate and a second pair of canting mechanisms associated with a second side of the backplate;

positioning an upper main belt and an upper secondary belt around a first portion of the user's body;

positioning a lower main belt and a lower secondary belt around a second portion of the user's body;

determining a desired length of each of the main belts based on the first and second portions of the user's body;

conforming each of the main belts to their determined desired lengths;

coupling a first end of each of the main and secondary belts to a corresponding canting mechanism;

allowing the upper main and secondary belts to adjust to conform to an underlying structure and natural conical shape of the first portion of the user's body through rotation of the corresponding canting mechanisms;

allowing the lower main and secondary belts to adjust to conform to an underlying structure and natural conical shape of the second portion of the user's body through rotation of the corresponding canting mechanisms;

securing the canting mechanisms to prevent further rotation of the canting mechanisms;

coupling a second end of the upper main belt to a second end of the upper secondary belt; and coupling a second end of the lower main belt to a second end of the lower secondary belt.

9. The method of claim 8, further comprising:
determining a length of each of the secondary belts based on the first and second portions of the user's body; and
conforming each of the secondary belts to their determined lengths.

10. The method of claim 8, wherein conforming each of the main belts to their determined lengths comprises cutting each of the main belts to their determined lengths.

11. The method of claim 8, further comprising rotating, before coupling the first end of each of the main and secondary belts to the corresponding canting mechanism, the corresponding canting mechanism about a corresponding pivot to allow each of the main and secondary belts to conform to the first and second portions of the user's body.

12. The method of claim 8, wherein coupling a first end of each of the main and secondary belts to the corresponding canting mechanism comprises:
placing the first end of each of the main and secondary belts within a receptacle of a buckle base; and
clamping down the first end of each of the main and secondary belts using a buckle lever hingedly coupled to the buckle base.

13. The method of claim 12, further comprising:
rotating, before the clamping step, the corresponding canting mechanism about the corresponding pivot to allow each of the main and secondary belts to conform to the first and second portions of the user's body; and
preventing rotation of each of the main and secondary belts via the clamping step.

14. The method of claim 13, wherein the clamping step comprises:
providing a first set of gear teeth on the buckle lever; and
meshing the first set of gear teeth with a second set of gear teeth associated with a buckle locking disc that is coupled to the backplate to prevent rotation of each of the main and secondary belts.

15. The method of claim 8, further comprising providing a pair of supports coupled between the upper main belt and the lower main belt, the supports limiting flexion of the user's body between the first and second portions of the user's body to a predetermined range.

16. The method of claim 8, wherein:
coupling a second end of the upper main belt to a second end of the upper secondary belt comprises securing the upper belt in one of a plurality of positions using a locking mechanism; and
coupling a second end of the lower main belt to a second end of the lower secondary belt comprises securing the lower belt in one of a plurality of positions using a locking mechanism.

17. The method of claim 8, wherein the first portion of the user's body is an upper portion of the user's torso below the user's ribs and the second portion of the user's body is a lower portion of the user's torso above the user's pelvic bones.

18. A canting system for a stabilization brace having two belts, comprising:
a backplate configured to be coupled between opposing ends of each of the belts; and
a plurality of canting mechanisms rotatably coupled to the backplate, each canting mechanism operable to couple an end of a corresponding belt to the backplate, each canting mechanism comprising:
a buckle base rotatably coupled to the backplate, the buckle base operable to receive the end of the corresponding belt and to allow the end to rotate about an associated pivot to allow the belt to conform to a portion of the user's body; and
a buckle lever coupled to the buckle base and operable to secure the end of the corresponding belt against the buckle base to prevent the buckle base from rotating once the belt has conformed to the portion of the user's body.

19. The canting system of claim 18, wherein the buckle lever is hingedly coupled to the buckle base.

20. The canting system of claim 18, further comprising a buckle locking disc coupled between the backplate and the buckle base, the buckle locking disc including a first set of gear teeth configured to mesh with a second set of gear teeth on the buckle lever when the buckle lever is in a closed position such that the buckle base is no longer able to rotate with respect to the backplate.

21. A stabilization brace, comprising:
an upper belt configured to be positioned around a portion of a user's body; and
a lower belt configured to be positioned around the portion of the user's body; and
one or more supports coupled between the upper and lower belts, each support comprising:
a housing having a first protuberance;
a piston slidably engaged with the housing, the piston having a second protuberance; and
an elastic member removably disposed about each of the first and second protuberances, the elastic member adapted to provide a resistance against flexion of the portion of the user's body.

22. The stabilization brace of claim 21 further comprising a motion limiter coupled to the housing, the support operable to limit flexion of the portion of the user's body to a predetermined range according to the position of the motion limiter.

23. The stabilization brace of claim 22 wherein the motion limiter is adjustably coupled to the housing in one of a plurality of predetermined positions.

24. The stabilization brace of claim 21 wherein the elastic member is formed from an elastomeric material and is loop-like in shape.

* * * * *